United States Patent [19]
Sulkowski

[11] 3,935,218
[45] Jan. 27, 1976

[54] IMIDAZOLINYL PHENYL CARBONYL COMPOUNDS ACID ADDITION SALTS AND RELATED COMPOUNDS

[75] Inventor: Theodore S. Sulkowski, Wayne, Pa.

[73] Assignee: American Home Products Corporation, New York, N.Y.

[22] Filed: Sept. 6, 1973

[21] Appl. No.: 394,708

Related U.S. Application Data

[60] Division of Ser. No. 757,792, Sept. 5, 1968, Pat. No. 3,763,178, which is a continuation-in-part of Ser. Nos. 622,918, March 14, 1967, abandoned, and Ser. No. 622,931, March 14, 1967, abandoned, and Ser. No. 576,833, Sept. 2, 1966, abandoned, and Ser. No. 487,587, Sept. 15, 1965, abandoned.

[52] U.S. Cl. .............................................. 260/309.6
[51] Int. Cl.² ......................................... C07D 49/34
[58] Field of Search ................................... 260/309.6

[56] References Cited
UNITED STATES PATENTS 3,717,658   2/1973   Metlesics et al. ................ 260/309.6

FOREIGN PATENTS OR APPLICATIONS
712,958   9/1968   Belgium .......................... 260/309.6

Primary Examiner—Ethel G. Love
Attorney, Agent, or Firm—Stephen Venetianer

[57] ABSTRACT

This invention is concerned with tetrahydropyrimidinyl phenyl carbonyl acid addition salts, imidazolinyl phenyl carbonyl acid addition salts, dihydroimidazoisoindolols, tetrahydropyrimidoisoindolols, and tetrahydropyrimidoisoindolol acid addition salts which are all pharmacologically efficacious as antidepressants. The tetrahydropyrimidinyl phenyl carbonyl acid addition salts, the tetrahydropyrimidoisoindolols and the tetrahydropyrimidoisoindolol acid addition salts are also efficacious as diuretics while the imidazolinyl phenyl carbonyl acid addition salts and the dihydroimidazoisoindolols are efficacious as anorexiants. This invention is also concerned with several processes for the preparation of these compounds.

2 Claims, No Drawings

IMIDAZOLINYL PHENYL CARBONYL COMPOUNDS ACID ADDITION SALTS AND RELATED COMPOUNDS

This is a division, of application Ser. No. 757,792, filed Sept. 5, 1968, now U.S. Pat. No. 3,763,178, which in turn is a continuation-in-part of U.S. Pat. applications, Ser. No. 622,918, entitled "Tetrahydropyrimidinyl Phenyl Carbonyl and Imidazolinyl Phenyl Carbonyl Compounds", filed Mar. 14, 1967; Ser. No. 622,931, entitled "Process For the Preparation of Imidazolinyl Phenyl Carbonyl compounds", filed March 14, 1967; Ser. No. 576,833, entitled "2-(3-Aminopropyl) Isoindoles and Related Compounds", filed Sept. 2, 1966; and Ser. No. 487,587, entitled "1,2,3,4,6,10b-Hexahydropyrimido[2,1-a]Isoindol-6-Ones and Related Compounds", filed Sept. 15, 1965, all now abandoned.

This invention relates to bicyclic and tricyclic nitrogen containing compounds as well as to novel methods for their preparation. In particular, the present invention is concerned with tetrahydropyrimidinyl phenyl carbonyl acid addition salts, tetrahydropyrimidoisoindolols and tetrahydropyrimidoisoindolol acid addition salts which in standard and accepted pharmacological tests have demonstrated both anti-depressant and diuretic activities. Further, it is concerned with imidazolinyl phenyl carbonyl acid addition salts and dihydroimidazoisoindolols which in standard and accepted pharmacological tests have demonstrated both anti-depressant and anorexiant activities.

The new and novel compounds which are included within the scope of this invention are represented by the following formulae:

group consisting of hydrogen, halogen, amino, lower alkylamino, lower alkyl and lower alkoxy; $R_3$ is hydrogen when $R_2$ and $R_3$ are dissimilar and when $R_2$ and $R_3$ are the same they are both selected from the group consisting of hydrogen, halogen, lower alkyl and lower alkoxy; $R_5$ is selected from the group consisting of phenyl, monohalophenyl, dihalophenyl, mono(lower)alkylphenyl, di(lower)alkylphenyl, trifluoromethylphenyl, mono(lower)alkoxyphenyl, di(lower)alkoxyphenyl, thienyl, pyridyl, furyl and tetrahydro-2-naphthyl; n is an integer from 1 to 2; and HX is a phramacologically acceptable acid addition salt. As employed herein the terms "lower alkyl","lower alkoxy" and the like are meant to include both branched and straight chain moieties containing from one to about six carbon atoms.

The new and novel compounds of this invention which are represented by structural formula (I) wherein n is 1 are called "Imidazolinyl Phenyl Carbonyl Acid Addition Salts". Typical examples thereof are: 2(2-imidazolin-2-yl) benzophenone hydrochloride and 4'-chloro-2-(imidazolin-2-yl)benzophenone hydrochloride. Alternatively, those compounds of structural formula (I) wherein $n$ is 2 are named: "Tetrahydropyrimidinyl Phenyl Carbonyl Acid Addition Salts", such as, 2-(3,4,5,6-tetrahydro-2-pyrimidinyl)-4-methylbutyrophenone hydrochloride and 2'-phenyl-2-(3,4,5,6-tetrahydro-2-pyrimidinylacetophenone hydrochloride.

The new and novel compounds of this invention which are depicted by structural formula (II) wherein n is 1 are designated "Dihydroimidazoisoindolols," for

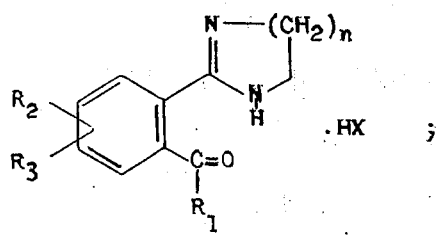

(I)

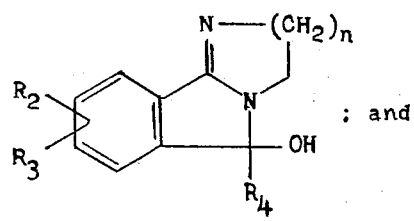

(II)

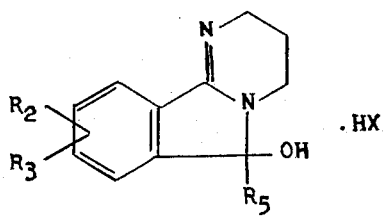

(III)

wherein $R_1$ and $R_4$ are selected from the group consisting of hydrogen, lower alkyl, phen(lower)alkyl, phenyl, monohalophenyl, dihalophenyl, mono(lower)alkylphenyl, di(lower)alkylphenyl, trifluoromethylphenyl, mono(lower)alkoxyphenyl, di(lower)alkoxyphenyl, thienyl, pyridyl, furyl and tetrahydro-2-naphthyl, with the provision that $R_1$ is hydrogen, lower alkyl and phen(lower)alkyl when n is 2; $R_2$ is selected from the example, 2,3-dihydro-5-phenyl-5H-imidazo[2,1-a]isoindol-5-ol and 5-(4-chlorophenyl)-2,3-dihydro-5H-imidazo[2,1-a]isoindol-5-ol. Alternatively, those compounds of structural formula (II) wherein n is 2 are called "Tetrahydropyrimidoisoindolos", such as, 6-(4-chlorophenyl)-2,3,4,6-tetrahydropyrimido[2,1-a] isoindol-6-ol and 2,3,4,6-tetrahydro-6-phenylpyrimido[2,1-a] isoindol-6-ol.

The new and novel compounds of this invention which are represented by structural formula (III) are named "Tetrahydropyrimidoisoindolol Acid Addition salts". Typical examples thereof are: 6-(4-chlorophenyl)-2,3,4,6-tetrahydropyrimido[2,1-a]isoindol-6-ol hydrochloride and 2,3,4,6-tetrahydro-6-phenyl-pyrimido[2,1-a]isoindol-6-ol hydrochloride.

In accord with the new and novel first process of this invention, the tetrahydropyrimidoisoindolols of this invention may be produced by the oxidation of 2-(3-aminopropyl)isoindoles, as exemplified by the following reaction scheme:

tively, the oxidation may be accomplished by contacting the 2-(3-aminopropyl) isoindole solution with an oxidzing agent, such as potassium dichromate, potassium chlorate, or potassim permanganate. The oxidation reaction may be conducted in any suitable reaction-inert solvent. Many such solvents will readily suggest themselves to one skilled in the art or organic chemistry.

When the aforesaid oxidation is complete, the product is separated by standard recovery methods, such as, concentration, filtration and crystallization. The tetrahydropyrimidoisoindolols (B) may then be recrystal-

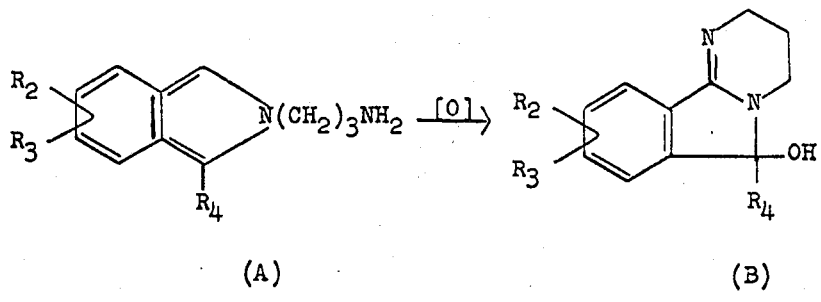

wherein $R_2$, $R_3$ and $R_4$ are defined as above. Various oxidation processes will readily suggest themselves to those skilled in the art. For example, the particular 2-(3-aminopropyl)isoindole (A) may be dissolved in a reaction-inert solvent, e.g. an alkanol, and purged with oxygen or air until the oxidation is complete. Alternalized from an appropriate solvent, such as dimethylformamide and dimethylacetamide.

In accord with the new and novel second process of the present invention, the dihydroimidazoisoindolols of this invention may be synthesized by the following schematic sequence of reactions:

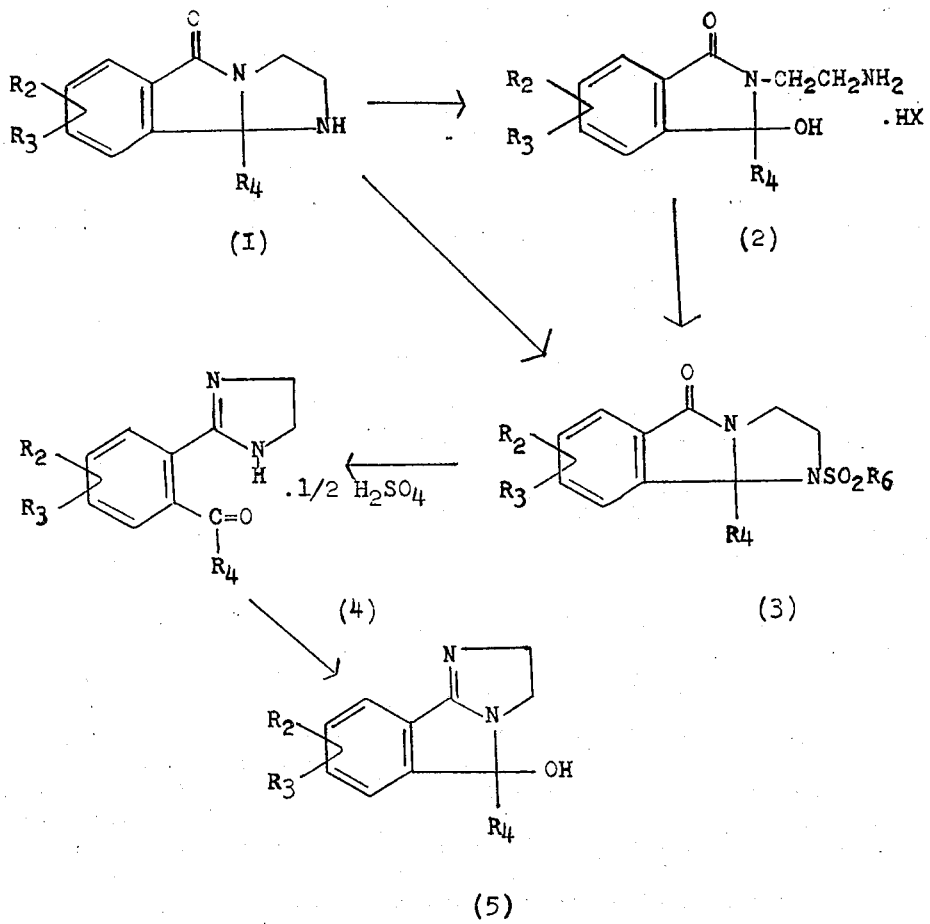

wherein $R_2$, $R_3$ and $R_4$ are defined as above, $R_6$ is aryl and alkyl, for example: lower alkyl, phenyl, monohalophenyl, dihalophenyl, mono(lower)alkylphenyl, di(lower)alkylphenyl and alkoxyphenyl, and X is the anion portion of a mineral acid. The rearrangement of a tetrahydroimidazoisoindolone of formula (1) is effected by contacting the particular compound (1) with a mineral acid. This reaction may be accelerated by heating and stirring the reaction mixture until the precipitation of the 2-(aminoethyl)-3-hydroxyphthalimidine mineral acid addition salt, as designated in formula (2), is complete. The phthalimidine (2) is separated by filtration or decantation and either recrystallized from a suitable solvent, such as water, a lower alkanol and dioxan, or admixed directly with a substantially equimolar quantity of an aryl or alkyl sulfonyl halide in pyridine. The reaction mixture is then heated to a temperature from about 80°C. to about 115°C. for a period from about two hours to about ten hours. Preferably, this reaction is conducted at the reflux temperature of the reaction mixture for a period of about two hours. After the above reaction is complete, the product of sulfonyltetrahydroimidazoisoindolone (3) is recovered by customary isolation procedures.

The above prepared sulfonyltetrahydroimidazoisoindolone (3) may be hydrolyzed and rearranged by admixture with from about 80 to about 100 percent sulfuric acid. The product of this hydrolysis, the sulfate salt of an imidazolinyl phenyl carbonyl compound, as shown in formula (4) which may be recovered as such by conventional means. Alternatively, the reaction mixture is neutralized by the addition of a base and the resulting precipitate recrystallized from an appropriate organic solvent such as lower alkanol, dioxan, dimethylformamide and dimethylacetamide to afford an appropriate dihydroimidazoisoindolol (5).

As a new and novel alternative to the second process of the present invention, it has been found that the dihydroimidazoisoindolols of this invention may also be prepared by directly reacting a tetrahydroimidazoisoindolone (1) with an aryl or alkyl sulfonyl halide under the above-described reaction conditions to afford an appropriate sulfonyltetrahydroimidazoisoindolone (3). Thereafter, this compound (3) is further reacted as hereinbefore described to yield an imidazolinyl phenyl carbonyl sulfate salt (4) which may then be neutralized to afford a dihydroimidazoisoindolol (5).

As a further alternative to the second process of the present invention, it should be noted that the 2-(aminoethyl)-3-hydroxyphthalimidine (2) intermediates can also be prepared by the condensation of an acid chloride of an o-carbonyl benzoic acid with ethylene diamine as described by Sulkowski et al. in J. Org. Chem. 32, 2180 (1967).

In accord with the new and novel third process of the present invention, some of the dihydroimidazoisoindolols of this invention may be prepared by the procedure which is exemplified by the following reaction scheme:

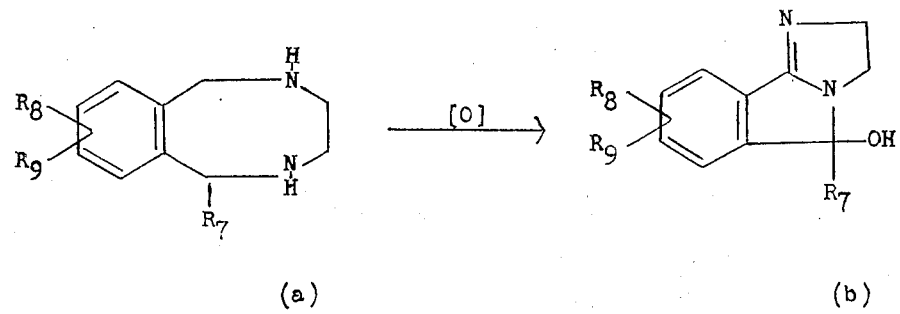

wherein $R_7$ is selected from the group consisting of lower alkyl, phenyl, lower alkylphenyl, lower alkoxyphenyl, di(lower)alkylphenyl, di(lower)alkoxyphenyl, aminophenyl, trifluoromethylphenyl, monohalophenyl, dihalophenyl, furyl, thienyl and naphthyl; $R_8$ is selected from the group consisting of hydrogen, halogen, lower alkyl and lower alkoxy; $R_9$ is hydrogen when $R_8$ and $R_9$ are dissimilar and when $R_8$ and $R_9$ are the same they are both selected from the group consisting of hydrogen, halogen, lower alkyl and lower alkoxy.

The oxidation reaction is effected by contacting an appropriate hexahydrobenzodiazocine (a) with an oxidizing agent in a reaction-inert solvent at a temperature from about 20°C. to about 60°C. for a period of about one-half to about four hours. Preferably, this reaction is conducted by contacting an aqueous solution of a hexahydrobenzodiazocine salt with a potassium permanganate solution at room temperature for about one hour. Many other oxidizing agents and reaction-inert solvents which may be employed in this reaction will readily suggest themselves to those skilled in the art. In this regard, excellent results can be obtained when potassium dichromate and potassium chlorate are employed as the oxidizing agents. By reaction-inert solvent as employed herein is meant a solvent which will dissolve the hexahydrobenzodiazocine and not interfere with the oxidation reaction, such as, water while acetone and methyl ethyl ketone may be employed as solvents when potassium permanganate is employed as the oxidizing agent.

When the oxidation reaction is complete, the corresponding dihydroimidazoisoindolol (b) may be separated and recovered by routine means, for example, precipitating the product by the addition of a base and then separating it by decantation or filtration. The time and temperature ranges employed in the aforesaid reactions are not critical but simply represent the most convenient range consistent with carrying out these reactions in a minimum of time without undue difficulty. Thus reaction temperatures appreciably below these can be used, but their use considerably extends the reaction time. Similarly, reaction temperatures higher than those mentioned can be employed with a concomitant decrease in reaction time. The 2-(3-aminopropyl)isoindoles (A) employed as starting materials in the first above described process for the preparation of the tetrahydropyrimidoisoindolol compounds (B) of this invention are known compounds which are described in co-pending United States patent application, Ser. No. 622,917, entitled "Isoindoles, Isoindolines and Related Compounds", filed on Mar. 14, 1967, by Theodore S. Sulkowski which is a continuation-in-part of United States patent applications, Ser. No. 576,833, entitled "2-(3-Aminopropyl)Isoindoles and Related Compounds", filed Sept. 2, 1966 and Ser. No. 487,587, entitled "1,2,3,4,6,10b-Hexahydropyrimido[2,1-a]Isoindol-6-Ones", filed Sept. 15, 1965 and now abandoned. The tetrahydroimidazoisoindolones (1) and the hexahydrobenzodiazocines (a) which are respectively employed as starting materials in the second and third above described process for the preparation of the dihydroimidazoisoindolols (5) of this invention are known compounds which are described in co-pending United States patent application, Ser. No. 609,779, entitled "Benzodiazocines", filed on Jan. 17, 1967, by Theodore S. Sulkowski, which is a continuation-in-part of United States patent applications, Ser. No. 554,672, entitled "Benzodiazocines", filed on June 2, 1966; Ser. No. 444,050, entitled "Substituted 3,4-Dihydro-6-Aryl-2,5-Benzodiazocin-1(2H)-Ones and Related Compounds", filed on Mar. 30, 1965 and now abandoned; and Ser. No. 272,216, entitled "Substituted 3,4-Dihydro-6-Aryl-2,5-Benzodiazocin-1(2H)-Ones and Related Compounds", filed on Apr. 11, 1963 and now abandoned. The aryl or alkyl sulfonyl chlorides used in this latter process are well known chemicals which are commercially available or may easily be prepared by well known chemical procedures.

The tetrahydropyrimidoisoindolols (B) of the present invention were at first thought to be "Hexahydropyrimidoisoindolones" and were so described in the first prior filed parent application (United States Ser. No. 487,587). Subsequently, these compounds were re-examined and then thought to be "Tetrahydropyrimidinyl Phenyl Carbonyl Compounds" and were so defined in the following two subsequently filed parent applications (U.S. Ser. Nos. 576,833 and 622,918). It has now been concluded, based on the nature of the starting materials; the mode of synthesis; the elemental analysis; and the ultra violet and infra red spectrographic analyses, that all the solid bases prepared by the first process of this invention are "Tetrahydropyrimidoisoindolols" (B). Further, since these nitrogen containing tetrahydropyrimidoisoindolols are basic in nature they will react with pharmacologically acceptable acids to form acid addition salts. Such acids are well known in the art, for example, hydrochloric, hydrobromic, hydroiodic, sulfuric, nitric, phosphoric, acetic, lactic, citric, tartaric, maleic, gluconic, benzenesulfonic, toluenesulfonic, methylsulfonic, ethylsulfonic acids and the like. These salts may be prepared by procedures commonly employed in the art, for example, reacting the compound with an equivalent of the selected acid in aqueous solution and concentration of the solution. Other known procedures may also be employed, e.g., the procedure of Example VIII.

The ultra violet spectrographic analyses of the tetrahydropyrimidoisoindolols (B) of this invention and their acid addition salts which are substituted in the 6-position with an aromatic group, e.g. phenyl, monohalophenyl, dihalophenyl, mono(lower)alkylphenyl, di(lower)alkylphenyl, trifluoromethylphenyl, mono(lower)alkoxyphenyl, di(lower)alkoxyphenyl, thienyl, pyridyl, furyl and tetrahydro-2-naphthyl, demonstrate an absence of absorption in the 250 m$\mu$ region indicating that both the bases and salts possess these tetrahydropyrimidoisoindol structures in solution. Alternatively, ultra violet analyses of neutral and acidic solutions of these tetrahydropyrimidoisoindolols (B) and their acid addition salts which are unsubstituted, e.g. hydrogen or substituted in the 6-position with an aliphatic or aralkyl group, e.g. lower alkyl and phen(lower)alkyl demonstrate absorption in the 235–240 m$\mu$ region indicating that their structures in solution are predominately the tetrahydropyrimidinyl phenyl carbonyl compounds of the structure:

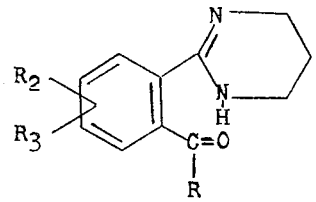

wherein $R_2$ and $R_3$ are defined as above and R is hydrogen, lower alkyl and phen(lower)alkyl. Further, the infra red spectrographic analyses of these latter compounds determined by the procedure of Hofmann et al., Analyt. Chem., Vol. 39, pg. 406 (1967) also indicates that the solid acid addition salts thereof also exist in the above shown tetrahydropyrimidinyl phenyl carbonyl forms.

The dihydroimidazoisoindolols (5) of the present invention were first thought to be "Tetrahydroimidazoindolones" and were so described in the first prior filed parent application. Subsequently, these compounds were re-examined and then thought to be "Imidazolinyl Phenyl Carbonyl Compounds" and were so defined in the following three subsequently filed parent applications (U.S. Ser. Nos. 576,833, 622,931 and 622,918). It has now been concluded, based on the nature of the starting materials; mode of synthesis; the elemental analysis; and ultra violet and infra red analyses, that all the solid bases prepared by the second and third process of this invention are "Dihydroimidazoisoindolols" (5). Further, since these nitrogen containing dihydroimidazoisoindolols are basic in nature they also will react with pharmacologically acceptable acids as described above to form acid addition salts.

The ultra violet spectrographic analyses of the dihydroimidazoisoindolols (5) of this invention in neutral solution demonstrate an absence of absorption in the 250 m$\mu$ region indicating that these bases also possess these dihydroimidazoisoindolol structures when they are dissolved in a non-acidic solution. Alternatively, the ultra violet analyses of acid solution of these bases and the neutral solutions of their acid addition salts demonstrate absorption in 250 m$\mu$ region indicating that they are imidazolinyl phenyl carbonyl compounds in solution of the structure:

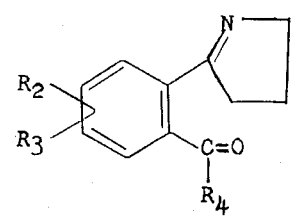

where $R_2$, $R_3$ and $R_4$ are defined as above. The infra red spectrographic analyses of these compounds also indicates that the solid bases are dihydroimidazoisoindolols while their corresponding solid acid addition salts exist in the above shown imidazolinyl phenyl carbonyl forms.

The tetrahydropyrimidinyl phenyl carbonyl acid addition salts (formula I where $n$ is 2); the tetrahydropyrimidoisoindolols (formula II where $n$ is 2); and the tetrahydropyrimidoisoindolol acid addition salts (formula III) of the present invention have been found to possess valuable pharmacological activity. More particularly, these compounds have exhibited utility, in standard pharmacological tests, as anti-depressant and diuretic agents.

In the pharmacological evaluation of the anti-depressent property of these compounds (I, $n=2$; II, $n=2$; and III), the in vivo anti-depressant activity is evaluated by the procedure described by Rubin et al., in J.P.E.T. 120, 125 (1957). When tested by this procedure, these compounds demonstrate useful anti-depressant activity, e.g. having mood elevating properties as psychic energizers, when they are administered orally to mice in a dosage range from about 1 to about 100 mg./kilo of animal body weight. Further, the in vivo diuretic activity of these compounds (I, $n=2$; II, $n=2$; and III) is evaluated by the procedure described by Lipschitz et al., in J. Pharacol. 79, 97 (1943). When tested by this procedure these compounds demonstrate useful diuretic activity when they are administered orally to rats in a dosage range from about 0.25 to about 25 mg./kilo of animal body weight.

The imidazolinyl phenyl carbonyl acid addition salts (formula I where $n$ is 1) and the dihydroimidazoisoindolols (formula II where $n$ is 1) of the present invention have also been found to possess valuable pharmacological activity. In particular, these compounds have exhibited utility, in standard pharmacological tests, as anti-depressant and anorexiant agents.

In the pharmacological evaluation of the anti-depressant property of these compounds (I, $n=1$ and II, $n=1$), the in vivo anti-depressant activity is also evaluated by the procedure described by Rubin et al., in J.P.E.T. 120, 125 (1957). When tested by this procedure, these compounds demonstrate useful anti-depressant activity e.g. having mood elevating properties as psychic energizers, when they are administered orally to mice in a dosage range from about 1 to about 5 mg./kilo of animal body weight. Further, the in vivo anorexiant activity of these compounds (I, $n=1$ and II, $n=1$), e.g. appetite suppressant effects is evaluated by the following procedure:

Male Charles River rats between 120 and 140 grams are trained to drink sweetened condensed milk from a graduated drinking tube. After a short learning period the animals are placed on a routine of water ad lib for 24 hours, standard laboratory chow for twenty-two hours and sweetened condensed milk for two hours. The volume of milk consumed is measured at one-half hour as well as two hours and the animals are weighed daily. This schedule is maintained five days a week over a period of several months. Trials are run on the same day each week and changes in milk consumed and twenty-four hour weight changes are compared to the average of the two days before the test compound is administered. Animals are tested as groups of six and one group is given saline each week to serve as controls. The test compounds are usually administered intraperitoneally in saline and/or orally in water.

The imidazolinyl phenyl carbonyl acid addition salts and the dihydroimidazoisoindolols of this invention in the above test procedure when administered orally to rats at a dose of 10 mg./kg. induce a decrease in food consumption of about 40 percent in the first half hour and about 20 percent in two hours with a concurrent total average weight loss of about one-half a gram/animal in 24 hours. When administered intraperitoneally at a dose of 10 mg./kg., these compounds (I, $n=1$ and II, $n=1$) induce a decrease in food consumption of about 80 percent in the first half hour and about 65 percent in two hours with a concurrent total 24 hour average weight loss of about seven and a half grams/animal.

When the tetrahydropyrimidinyl phenyl carbonyl acid addition salts; the tetrahydropyrimidoisoindolols and the tetrahydropyrimidoisoindolol acid addition salts of this invention are employed as anti-depressant and diuretic agents and when the imidazolinyl phenyl carbonyl acid addition salts and the dihydroimidazoisoindolols of this invention are employed as anti-depressant and anorexiant agents, they may be administered to mammals, e.g. mice, rats, rabbits, dogs, cats, monkeys, etc. alone or in combination with pharmacologically acceptable carriers, the proportion of which is determined by the solubility and chemical nature of the compound, chosen route of administration and standard biological practice. For example, they may be administered orally in the solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the compounds of this invention will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects.

The following examples are given by way of illustration and are not to be construed as limitations of this invention, many variations of which are possible without departing from the scope and spirit thereof.

EXAMPLE I

The 2-(3-aminopropyl)-1-(4-chlorophenyl)isoindole, hydrochloride (2 gms.) is dissolved in water and neutralized with a sodium carbonate solution. The regenerated base is extracted with ethyl acetate, dried over magnesium sulfate and evaporated to dryness. The residue is dissolved in 250 ml. of ethanol and air is bubbled through the solution for 48 hours. The precipitated white crystalline solid is separated by filtration and upon recrystallization from dimethylformamide there is obtained 6-(4-chlorophenyl)-2,3,4,6-tetrahydropyrimido[2,1-a]isoindol-6-ol, m.p. 274°-6°C. dec., which is insoluble in water and soluble in dimethylacetamide.

Analysis: Ultra Violet Absorption (95% ETOH) max. 224 mµ (ε=23,000), infl. 243 mµ (ε=12,000), max. 267 mµ (ε=3,800); Ultra Violet Absorption (pH1) max. 223 mµ (ε=21,100), infl. 243 mµ (ε=14,200), max. 267 mµ(ε=3,800); Infra Red Absorption (KBr) 1652 cm$^{-1}$, 2400–3000cm$^{-1}$.

Calc'd for $C_{17}H_{15}ClN_2O$: C, 68.33; H, 5.06; N, 9.33; Cl, 11.87. Found: C, 68.12; H, 5.39; N, 9.22; Cl, 11.85.

The above prepared tetrahydropyrimidoisoindolol is dissolved in ethanol and admixed with an aqueous solution containing an equivalent amount of hydrochloric acid. The mixture is stirred for ten minutes and the solvent removed by evaporation. In this manner, is obtained 6-(4-chlorophenyl)-2,3,4,6-tetrahydropyrimido[2,1-a]isoindol-6-ol hydrochloride, m.p. 232°-4°C., as a white crystalline solid, which is soluble in hot water.

Analysis: Ultra Violet Absorption (95% ETOH) max. 224 mµ(ε=23,000), infl. 243 mµ(ε=14,000), infl. 268 mµ (ε=3,800); Infra Red Absorption (KBr) 1675 cm$^{-1}$, 2600–3300 cm$^{-1}$.

Calc'd for $C_{17}H_{15}ClN_2O \cdot HCl$: C, 60.91; H, 4.81; N, 8.36; Cl, 21.16. Found: C, 60.91; H, 5.06; N, 8.31; Cl, 21.1.

EXAMPLE II

The procedure of Example I is repeated reacting an appropriate 2-(3-aminopropyl)isoindole with an oxidizing agent, e.g. potassium dichromate, potassium chlorate and hydrogen peroxide to afford the hereinafter listed products:

| 2-(3-AMINOPROPYL)ISOINDOLES | PRODUCTS |
|---|---|
| 2-(3-aminopropyl)-6-bromo-1-(4-tolyl)isoindole | 8-bromo-2,3,4,6-tetrahydro-6-(4-tolyl)pyrimido[2,1-a]isoindol-6-ol |
| 2-(3-aminopropyl)-5-methyl-1-propylisoindole | 2,3,4,6-tetrahydro-9-methyl-6-propylpyrimido[2,1-a]isoindol-6-ol |
| 2-(3-aminopropyl)-4-iodoisoindole | 2,3,4,6-tetrahydro-10-iodopyrimido[2,1-a]isoindol-6-ol |
| 2-(3-aminopropyl)-1-(4-bromophenyl)-5,6-dibromoisoindole | 8,9-dibromo-6-(4-bromophenyl)-2,3,4,6-tetrahydropyrimido[2,1-a]isoindol-6-ol |
| 2-(3-aminopropyl)-1-(2,4-dimethoxyphenyl)isoindole | 2,3,4,6-tetrahydro-6-(2,4-dimethoxyphenyl)pyrimido[2,1-a]isoindol-6-ol |

EXAMPLE III

Ten grams of 10B-phenyl-1,2,3,4,6,10b-hexahydropyrimido[2,1-a]isoindol-6-one are added in portions to a stirred suspension of 2.5 grams of lithium aluminum hydride in 250 ml. of anhydrous ether. The mixture is stirred and refluxed for one hour, then the excess hydride is decomposed by careful addition of water. The ether layer is separated, dried over magnesium sulfate and evaporated to dryness. Without isolation or further purification, the 2-(3-aminopropyl)-1-phenylisoindole is dissolved in 200 ml. of ethanol and oxygen is bubbled through the solution for 48 hours. The precipitated solid is separated by filtration and on recrystallization from dimethylformamide there is obtained 2,3,4,6-tetrahydro-6-phenylpyrimido[2,1-a]isoindol-6-ol, m.p. 255°-7°C. dec., as white prisms which is insoluble in water and slightly soluble in hot dimethylacetamide.

Analysis: Ultra Violet Absorption (95% ETOH) max. 233 mµ (ε=14,000), max. 268 mµ (ε=4,000), infl. 271 mµ (ε=3,000); Ultra Violet Absorption (pH1) max. 239 mµ (ε=14,900), infl. 271 mµ (ε=3,000); Infra Red Absorption (KBr) 1650 cm$^{-1}$, 2300–3000 cm$^{-1}$.

Calc'd for $C_{17}H_{16}N_2O$: C, 77.25; H, 6.10; N, 10.60. Found: C, 77.36; H, 6.05; N, 10.51.

The above reaction is repeated in anhydrous diisopropyl ether at 60°C. for two hours with similar results.

In a similar manner, starting with 10b-(3',4'-dichlorophenyl)-1,2,3,4,6,10b-hexahydropyrimido[2,1-a]isoindol-6-one there is obtained 6-(3,4-dichlorophenyl)-2,3,4,6-tetrahydropyrimido[2,1-a]isoindol-6-ol, m.p. 267°-9°C., as a white crystalline solid which is insoluble in water and slightly soluble in hot dimethylacetamide.

Analysis: Ultra Violet Absorption (95% ETOH) infl. 230 mµ (ε = 22,600), max. 268 mµ (ε=4,5000); infl. 282 mµ (ε = 2,000); Ultra Violet Absorption (pH1) max. 228 mµ (ε = 22,000), max. 268 mµ (ε = 4,700); infl. 282 mµ (ε = 1,600); Infra Red Absorption (KBr) 1650 cm$^{-1}$, 2300–3000 cm$^{-1}$.

Calc'd for $C_{17}H_{14}Cl_2N_2O$: C, 61.27; H, 4.24; N, 8.41; Cl, 21.29. Found: C, 61.41; H, 4.28; N, 8.46; Cl, 21.2.

EXAMPLE IV 2-(3-Aminopropyl)-1-(4-bromophenyl)isoindole (4.0 gms.) is dissolved in 100 ml. of ethanol and oxidized by bubbling oxygen through the solution for 36 hours. The precipitated solid is separated by decantation and recrystallized from dimethylformamide. In this manner, is obtained 6-(4-bromophenyl)-2,3,4,6-tetrahydropyrimido[2,1-a]isoindol-6-ol, m.p. 278°-9°C. dec., as a white crystalline solid which is insoluble in water and slightly soluble in dimethylacetamide Analysis: Ultra Violet Absorption (95% ETOH) max. 228 mµ (ε=22,500), max. 267 mµ (ε=4,300); Ultra Violet Absorption (pH1) max. 229 mµ (ε=21,500), max. 267 mµ (ε=4,300); Infra Red Absorption (KBr) 1645 cm$^{-1}$, 2300–2900 cm$^{-1}$.

Calc'd for $C_{17}H_{15}BrN_2O$: C, 59.48; H, 4.41; N, 8.16. Found: C, 59.51; H, 4.36; N, 8.26.

Similarly, utilizing anhydrous ethylene glycol dimethyl ether as the solvent, 6-(2,4-dibromophenyl)-2,3,4,6-tetrahydropyrimido[2,1-a]isoindol-6-ol is synthesized.

EXAMPLE V 2-(3-Aminopropyl)-1-(5',6',7',8'-tetrahydro-2'-naphthyl)isoindole (3.0 gms.) is dissolved in 250 ml. of benzene and oxidized by bubbling oxygen through the solution for 60 hours. The precipitate is separated by filtration and recrystallized from dimethylacetamide. In this manner, is obtained 6-(5,6,7,8-tetrahydro-2-naphthyl)-2,3,4,6-tetrahydropyrimido[2,1-a]isoindol-6-ol, m.p. 253–5°dec., as a white crystalline solid which is insoluble in water and soluble in hot dimethylacetamide.

Analysis: Ultra Violet Absorption (95% ETOH) infl. 230 mµ (ε=10,000), infl. 245 mµ (ε=9,200), max. 270 mµ (ε=3,200); Ultra Violet Absorption (pH1) infl. 230 mµ (ε=10,900), infl. 245 mµ (ε=10,000), max. 270 mµ (ε=3,200); Infra Red Absorption (KBr) 1655 cm$^{-1}$, 2300–3000 cm$^{-1}$.

Calc'd for $C_{21}H_{22}N_2O$: C, 79.21; H, 6.96; N, 8.80. Found: C, 78.96; H, 7.15; N, 8.95.

In a similar manner, 6-(4-trifluoromethylphenyl)-2,3,4,6-tetrahydropyrimido[2,1-a]isoindol-6-ol; 6-(2-trifluoromethylphenyl)-2,3,4,6-tetrahydropyrimido[2,1-a]isoindol-6-ol; and 6-furyl-2,3,4,6-tetrahydropyrimido[2,1-a]isoindol-6-ol are produced.

EXAMPLE VI

Repeating the procedure of Example V but starting with 2-(3-aminopropyl)-1-methylisoindole, there is obtained 2,3,4,6-tetrahydro-6-methylpyrimido[2,1-a]isoindol-6- -ol, m.p. 199°–201°C., as a white crystalline solid which is insoluble in water and soluble in dimethylacetamide.

Analysis: Ultra Violet Absorption (95% ETOH) max. 236 m$\mu$ ($\epsilon$ = 12,600), infl. 265 m$\mu$ ($\epsilon$ = 4,100); Ultra Violet Absorption (pH1) max. 239.5 m$\mu$ ($\epsilon$ = 14,200), infl. 265 m$\mu$ ($\epsilon$ = 4,100); Infra Red Absorption (KBr), 1640 cm$^{-1}$, 2300–3000 cm$^{-1}$; Infra Red Absorption of the in situ hydrochloride salt by the procedure of Hofmann et al., Analyt. Chem. Vol. 39, pg. 406 (1967) (KBr) 1670 cm$^{-1}$, 1647 cm$^{-1}$, 2600–3100 cm$^{-1}$.

Calc'd for $C_{12}H_{14}N_2O$: C, 71.26; H, 6.98; N, 13.87. Found: C, 71.30; H, 6.90; N, 13.63

In a similar manner, the following compounds are prepared:

2,3,4,6-Tetrahydropyrimido[2,1-a]isoindol-6-ol, m.p. 205°–7°C., as a white crystalline sold which is insoluble in water and slightly soluble in dimethylacetamide.

Analysis: Ultra Violet Absorption (95% ETOH) max. 235 m$\mu$ ($\epsilon$ = 12,400), infl. 266.5 m$\mu$ ($\epsilon$ = 3,650); Ultra Violet Absorption (pH1) max. 240 m$\mu$ ($\epsilon$ = 10,800), infl. 266.5 m$\mu$ ($\epsilon$ = 3,650); Infra Red Absorption (KBr) 1640 cm$^{-1}$, 2300–3000 cm$^{-1}$; Infra Red Absorption of the in situ hydrochloride by the above-identified procedure (KBr) 1670 cm$^{-1}$, 2600–3100 cm$^{-1}$.

Calc'd for $C_{11}H_{12}N_2O$: C, 70.18; H, 6.42; N, 14.88. Found: C, 69.92; H, 6.47; N, 14.71.

6-Benzyl-2,3,4,6-tetrahydropyrimido[2,1-a]isoindol-6-ol, m.p. 233°–5°C. dec., as a white. cyrstalline solid which is insoluble in water.

Analysis: Ultra Violet Absorption (95% ETOH) max. 235 m$\mu$ ($\epsilon$ = 11,700), infl. 269 m$\mu$ ($\epsilon$ = 3,900); Ultra Violet Absorption (pH1) max. 240 m$\mu$ ($\epsilon$ = 12,900), infl. 269 m$\mu$ ($\epsilon$ = 3,900); Infra Red Absorption (KBr) 1645 cm$^{-1}$, 2300–3000 cm$^{-1}$; Infra Red Absorption of the in situ hydrochloride by the above-identified procedure (KBr) 1665 cm$^{-1}$, 2600–3100 cm$^{-1}$.

Calc'd for $C_{18}H_{18}N_2O$: C, 77.66; H, 6.52; N, 10.07. Found: C, 77.67; H, 6.41; N, 9.77.

6-Butyl-2,3,4,6-tetrahydropyrimido[2,1-a]isoindol-6-ol, m.p. 181°–3°C., as a white crystalline solid which is insoluble in water and soluble in ethanol and dimethylacetamide.

Analysis: Ultra Violet Absorption (95% ETOH) max. 234.5 m$\mu$ ($\epsilon$ = 12,100), infl. 266 m$\mu$ ($\epsilon$ = 4,000); Ultra Violet Absorption (pH1) max. 240 m$\mu$ ($\epsilon$ = 14,000), infl. 266 m$\mu$ ($\epsilon$ = 4,000); Infra Red Absorption (KBr) 1640 cm$^{-1}$, 2300–3000 cm$^{-1}$; Infra Red Absorption of the in situ hydrochloride by the above-identified procedure (KBr) 1670 cm$^{-1}$, 1640 cm$^{-1}$, 2600–3100 cm$^{-1}$.

Calc'd for $C_{15}H_{20}N_2O$: C, 73.73; H, 8.25; N, 11.47. Found: C, 74.03; H, 7.99; N, 11.63.

6-(3-Amino-4-chlorophenyl)-2,3,4,6-tetrahydropyrimido[2,1-a]isoindol-6-ol, m.p. 227°–8°C. dec., as a white crystalline solid which is insoluble in water and soluble in hot dimethylacetamide.

Analysis: Calc'd for $C_{17}H_{16}ClN_3O$: C, 65.05; H, 5.14; N, 13.39. Found: C, 65.09; H, 5.49; N, 13.61.

2,3,4,6-Tetrahydro-6-(4-tolyl)-pyrimido[2,1-a]isoindol-6-ol, m.p. 237°–9°C., dec., as a white crystalline solid which is insoluble in water and soluble in dimethylacetamide.

Analysis: Calc'd for $C_{18}H_{18}N_2O$: C, 77.67; H, 6.52; N, 10.07. Found: C, 77.62; H, 6.48; N, 9.94.

EXAMPLE VII

When the procedure of the aforementioned Examples is employed, the hereinafter listed 2-(3-aminopropyl)phenylisoindoles are oxidized to afford the following products:

| 2-(3-AMINOPROPYL) PHENYLISOINDOLES | TETRAHYDROPYRIMIDO- ISOINDOLOLS |
|---|---|
| 2-(3-aminopropyl)-6-chloro-1-phenylisoindole | 8-chloro-2,3,4,6-tetrahydro-6-phenylpyrimido[2,1-a]isoindol-6-ol |
| 2-(3-aminopropyl)-5-methyl-1-phenylisoindole | 2,3,4,6-tetrahydro-9-methyl-6-phenylpyrimdio[2,1-a]isoindol-6-ol |
| 2-(3-aminopropyl)-6-ethylamino-1-phenylisoindole | 8-ethylamino-2,3,4,6-tetrahydro-6-phenylpyrimido[2,1-a]isoindol-6-ol |
| 2-(3-aminopropyl)-5,6-dichloro-1-phenylisoindole | 8,9-dichloro-2,3,4,6-tetrahydro-6-phenylpyrimido[2,1-a]isoindol-6-ol |
| 2-(3-aminopropyl-5,6-dimethoxy-1-phenylisoindole | 2,3,4,6-tetrahydro-8,9-dimethoxy-6-phenylpyrimido[2,1-a]isoindol-6-ol |
| 2-(3-aminopropyl)-1-(3,4-diiodophenyl)isoindole | 2,3,4,6-tetrahydro-6-(3,4-diiodophenyl)pyrimido[2,1-a]isoindol-6-ol |
| 2-(3-aminopropyl)-1-isopropyl-5,6-dipropoxyisoindole | 2,3,4,6-tetrahydro-6-isopropyl-8,9-dipropoxypyrimido[2,1-a]isoindol-6-ol |
| 2-(3-aminopropyl)-1-(3,4-diethoxyphenyl)isoindole | 6-(3,4-diethoxyphenyl-2,3,4,6-tetrahydropyrimido[2,1-a]isoindol-6-ol |
| 2-(3-aminopropyl)-1-(4-hexylphenyl)isoindole | 6-(4-hexylphenyl)-2,3,4,6-tetrahydropyrimido[2,1-a]isoindol-6-ol |
| 5-amino-2-(3-aminopropyl)isoindole | 9-amino-2,3,4,6-tetrahydropyrimido[2,1-a]isoindol-6-ol |

| 2-(3-AMINOPROPYL) PHENYLISOINDOLES | TETRAHYDROPYRIMIDO-ISOINDOLOLS |
|---|---|
| 5-chloro-1-(4-ethylphenyl) isoindole | 9-chloro-6-(4-ethylphenyl)-2,3,4,6-tetrahydropyrimido[2,1-a]isoindol-6-ol |
| 2-(3-aminopropyl)-1-(2-thienyl)isoindole | 2,3,4,6-tetrahydro-6-(2-thienyl)pyrimido[2,1-a]isoindol-6-ol |
| 2-(3-aminopropyl)-5--methyl-1-phenylisoindole | 2,3,4,6-tetrahydro-9-methyl-6-phenylpyrimido[2,1-a]isoindol-6-ol |
| 2-(3-aminopropyl)-1-phenyl-7-propylisoindole | 2,3,4,6-tetrahydro-6-phenyl-7-propylpyrimido[2,1-a]isoindol-6-ol |
| 2-(3-aminopropyl)-1-(4-fluorophenyl(isoindole | 6-(4-fluorophenyl)-2,3,4,6-tetrahydropyrimido[2,1-a]isoindol-6-ol |
| 2-(3-aminopropyl)-1-(3-bromo-4-methylphenyl)isoindole | 6-(3-bromo-4-methylphenyl)-2,3,4,6-tetrahydropyrimido[2,1-a]isoindol-6-ol |
| 2-(3-aminopropyl)-1-(3-iodophenyl)isoindole | 2,3,4,6-tetrahydro-6-(3-iodophenyl)pyrimido[2,1-a]isoindol-6-ol |
| 2-(3-aminopropyl)-5-amyl-1-phenylisoindole | 9-amyl-2,3,4,6-tetrahydro-6-phenylpyrimido[2,1-a]isoindol-6-ol |
| 2-(3-aminopropyl)-1-phenyl-6-propylaminoisoindole | 2,3,4,6-tetrahydro-6-phenyl-8-propylaminopyrimido[2,1-a]isoindol-6-ol |
| 2-(3-aminopropyl)-5-butoxy-1-phenylisoindole | 9-butoxy-2,3,4,6-tetrahydro-6-phenylpyrimido[2,1-a]isoindol-6-ol |
| 2-(3-aminopropyl)-1-(3,4-dimethylphenyl)isoindole | 2,3,4,6-tetrahydro-6-(3,4-dimethylphenyl)pyrimido[2,1-a]isoindol-6-ol |
| 2-(3-aminopropyl)-1-(4-propoxyphenyl)isoindole | 2,3,4,6-tetrahydro-6-(4-propoxyphenyl)pyrimido[2,1-a]isoindol-6-ol |
| 2-(3-aminopropyl)-5,6-dimethylisoindole | 2,3,4,6-tetrahydro-8,9-dimethylpyrimido[2,1-a]isoindol-6-ol |
| 2-(3-aminopropyl)-1-pyridiyl-isoindole | 2,3,4,6-tetrahydro-6-pyridylpyrimido[2,1-a]isoindol-6-ol |
| 2-(3-aminopropyl)-1-butyl-5-methoxyisoindole | 6-butyl-2,3,4,6-tetrahydro-9-methoxypyrimido[2,1-a]isoindol-6-ol |

EXAMPLE VIII

Ten grams of 2,3,4,6-tetrahydro-6-(2-thienyl)pyrimido[2,1-a]isoindol-6-ol, as described in Example VII, are suspended in 75 ml. of absolute ethanol and then saturated with a continuous flow of hydrochloric acid gas. The resulting solution is evaporated to dryness and ethanol-ethylacetate to yield 2,3,4,6-tetrahydro-6-(2-thienyl)pyrimido[2,1,-a]isoindol-6-ol hydrochloride, m.p. 238°C. dec., as a white crystalline solid which is soluble in water.

Analysis: Calc'd for $C_{15}H_{14}N_2OS \cdot HCl$: C, 58.71; H, 4.93; N, 9.14; Cl, 11.56; S, 10.45 Found: C, 58.77; H, 4.74; N, 9.20; Cl, 11.75; S, 10.8.

EXAMPLE IX

When the procedure of Example VIII is repeated with the tetrahydropyrimidoisoindolols of Examples II - VII, the following respective hydrochloride salts are obtained:

8-bromo-2,3,4,6-tetrahydro-6-(4-tolyl)pyrimido[2,1-a]isoindol-6-ol hydrochloride;
2(3,4,5,6-tetrahydro-2-pyrimidinyl)-4-methylbutyrophenone hydrochloride;
2-(3,4,5,6-tetrahydro-2-pyrimidinyl)-3-iodobenzaldehyde hydrochloride;
8,9-dibromo-6-(4-bromophenyl)-2,3,4,6-tetrahydropyrimido[2,1-a]isoindol-6-ol hydrochloride;
2,3,4,6-tetrahydro-6-(2,4-dimethoxyphenyl)-pyrimido[2,1-a]isoindol-6-ol hydrochloride;
2,3,4,6-tetrahydro-6-phenylpyrimido[2,1-a]isoindol-6-ol hydrochloride;
6-(3,4-dichlorophenyl)-2,3,4,6-tetrahydropyrimido[2,1-a]isoindol-6-ol hydrochloride;
6-(4-bromophenyl)-2,3,4,6-tetrahydropyrimido[2,1-a]isoindol-6-ol hydrochloride;
6-(2,4-dibromophenyl)-2,3,4,6-tetrahydropyrimido[2,1-a]isoindol-6-ol hydrochloride;
6-(5,6,7,8-tetrahydro-2-naphthyl)-2,3,4,6-tetrahydropyrimido[2,1-a]isoindol-6-ol hydrochloride;
6-(4-trifluoromethylphenyl)-2,3,4,6-tetrahydropyrimido[2,1-a]isoindol-6-ol hydrochloride;
6-(2-trifluoromethylphenyl)-2,3,4,6-tetrahydropyrimido[2,1-a]isoindol-6-ol hydrochloride;
6-furyl-2,3,4,6-tetrahydropyrimido[2,1-a]isoindol-6-ol hydrochloride;
2-(3,4,5,6-tetrahydro-2-pyrimidinyl)acetophenone hydrochloride;
2-(3,4,5,6-tetrahydro-2-pyrimidinyl)benzaldehyde hydrochloride;
2'-phenyl-2-(3,4,5,6-tetrahydro-2-pyrimidinyl) acetophenone hydrochloride;
2-(3,4,5,6-tetrahydro-2-pyrimidinyl)valerophenone hydrochloride
6-(3-amino-4-chlorophenyl)-2,3,4,6-tetrahydropyrimido[2,1-a]isoindol-6-ol hydrochloride;
2,3,4,6-tetrahydro-6-(4-tolyl)pyrimido[2,1-a]isoindol-6-ol hydrochloride;
8-chloro-2,3,4,6-tetrahydro-6-phenylpyrimido[2,1-a]isoindol-6-ol hydrochloride;
2,3,4,6-tetrahydro-9-methyl-6-phenylpyrimido[2,1-a]isoindol-6-ol hydrochloride;

8-ethylamino-2,3,4,6-tetrahydro-6-phenyl-pyrimido[2,1-a]isoindol-6-ol dihydrochoride;

8,9-dichloro-2,3,4,6-tetrahydro-6-phenyl-pyrimido[2,1-a]isoindol-6-ol hydrochloride;

2,3,4,6-tetrahydro-8,9-dimethoxy-6-phenyl-pyrimido[2,1-a]isoindol-6-ol hydrochloride;

2,3,4,6-tetrahydro-6-(3,4-diiodophenyl)-pyrimido[2,1-a]isoindol-6-ol hydrochloride;

2-(3,4,5,6-tetrahydro12-pyrimidinyl)-2'-methyl-4,5-dipropoxypropiophenone hydrochloride;

6-(3,4-diethoxyphenyl)-2,3,4,6-tetrahydropyrimido[2,1-a]isoindol-6-ol hydrochloride;

6-(4-hexylphenyl)-2,3,4,6-tetrahydropyrimido[2,1-a]isoindol-6-ol hydrochloride;

4-amino-2-(3,4,5,6-tetrahydro-2-pyrimidinyl)benzaldehyde dihydrochloride;

9-chloro-6-(4-ethylphenyl)-2,3,4,6-tetrahydropyrimido]2,1-a]isoindol-6-ol hydrochloride;

2,3,4,6-tetrahydro-6-(2-thienyl)pyrimido[2,1-a]isoindol-6-ol hydrochloride;

2,3,4,6-tetrahydro-9-methyl-6-phenylpyrimido[2,1-a]isoindol-6-ol hydrochloride;

2,3,4,6-tetrahydro-6-phenyl-7-propylpyrimido[2,1-a]isoindol-6-ol hydrochloride;

6-(4-fluorophenyl)-2,3,4,6-tetrahydropyrimido[2,1-a]isoindol-6-ol hydrochloride;

6-(3-bromo-4-methylphenyl)-2,3,4,6-tetrahydropyrimido[2,1-a]isoindol-6-ol hydrochloride;

2,3,4,6-tetrahydro-6-(3-iodophenyl)pyrimido[2,1-a]isoindol-6-ol hydrochloride;

9-amyl-2,3,4,6-tetrahydro-6-phenylpyrimido[2,1-a]isoindol-6-ol hydrochloride;

2,3,4,6-tetrahydro-6-phenyl-8-propylaminopyrimido[[2,1-a]isoindol-6-ol dihydrochloride;

9-butoxy-2,3,4,6-tetrahydro-6-phenylpyrimido[2,1-a]isoindol-6-ol hydrochloride;

2,3,4,6-tetrahydro-6-(3,4-dimethylphenyl)-pyrimido[2,1-a]isoindol-6-ol hydrochloride;

2,3,4,6-tetrahydro-6-(4-propoxyphenyl)-pyrimido[2,1-a]isoindol-6-ol hydrochloride;

2-(3,4,5,6-tetrahydro-2-pyrimidinyl)-4,5-dimethylbenzaldehyde hydrochloride;

2,3,4,6-tetrahydro-6-pyridylpyrimido[2,1-a]isoindol-6-ol hydrochloride; and 2-(3,4,5,6-tetrahydro-2-pyrimidinyl)-4-methoxyvalerophenone hydrochloride.

EXAMPLE X

Thirty-five grams of 9b-(p-chlorophenyl)-1,2,3,9b-tetrahydro-1H-imidazo[2,1-a]isoindol-5-one and 150 ml. of 60 percent hydrochloric acid are stirred and heated to a clear solution. Stirring is continued for 20 minutes after solid begins to precipitate. The mixture is cooled and the solid is separated by filtration. On recrystallization from ethanol there is obtained 2-(2-aminoethyl)-3-(p-chlorophenyl)-3-hydroxyphthalimidine hydrochloride, m.p. 243°–5°C.

Analysis: Calc'd for $C_{16}H_{15}N_2OCl \cdot HCl$: C, 56.63; H, 4.76; N, 8.26; Cl, 20.91. Found: C, 56.38; H, 4.57; N, 8.01; Cl, 20.9.

Seventeen grams of the phthalimidine hydrochloride from above, 20 g. of p-toluenesulfonyl chloride and 200 ml. of pyridine are refluxed for two hours and then the mixture is evaporated to dryness. On recrystallization of the residue from ethanol there is obtained 9b-(p-chlorophenyl)- 1,2,3,9b-tetrahydro-1-(p-tolylsulfonyl)-1H-imidazo[2,1-a]isoindol-5-one, m.p. 170°–2°C.

Analysis: Calc'd for $C_{23}H_{19}ClN_2O_3S$: C, 62.93; H, 4.34; N, 6.38; Cl, 8.08; S, 7.30. Found: C, 63.24; H, 4.61; N, 6.15; Cl, 7.91; S, 7.3.

Ten grams of 9b-(p-chlorophenyl)-1,2,3,9b-tetrahydro-1-(p-tolylsulfonyl)-1H-imidazo[2,1-a]isoindol-5-one are dissolved in 25 ml. of 90 percent sulfuric acid and stirred at room temperature for one-half hour. The solution is quenched with ice water, then filtered to separate some precipitated solid. The filtrate which contains the sulfate salt of 4'-chloro-2-(2-imidazolin-2-yl)benzophenone is cooled and made basic with a saturated sodium bicarbonate solution. The precipitated solid is separated by filtration and washed throughly with water. On recrystallization from ethanol there is obtained 5-(4-chlorophenyl)-2,3-dihydro-5H-imidazo[2,1-a]isoindol-5-ol, m.p. 215°–7°C., dec., as a white crystalline solid which is insoluble in water and soluble in ethanol.

Analysis: Ultra Violet Absorption (95% ETOH) max. 223 m$\mu$ ($\epsilon$=19,000), infl. 242.5 m$\mu$ ($\epsilon$=8,300), max. 268.5 m$\mu$ ($\epsilon$=4,400), max. 272 m$\mu$ ($\epsilon$=4,400); Ultra Violet Absorption (pH1) infl. 223 m$\mu$($\epsilon$=18,000), max. 251 m$\mu$ ($\epsilon$=11,000), max. 253 m$\mu$ ($\epsilon$=10,800); Infra Red Absorption (KBr) 1647 cm$^{-1}$, 2300–3200 cm$^{-1}$.

Calc'd for $C_{16}H_{13}N_2OCl$: C, 67.49; H, 4.60N, 9.40; Cl, 12.45. Found: C, 67.18; H, 4.32; N, 9.68; Cl, 12.7.

In a similar manner, the sulfate salts of 2-(2-imidazolin-2-yl)-3',4'-diiodobenzophenone; 2'-(2-imidazolin-2-yl)-2-methyl-4',5'-dipropoxypropiophenone and 3',-4'-diethoxy-2-(2-imidazolin-2-yl)benzophenone are produced which are then contacted with a saturated sodium bicarbonate solution to respectively afford the following compounds: 2,3-dihydro-5-(3,4-diiodophenyl)-5H-imidazo[2,1-a]isoindol-5-ol; 2,3-dihydro-5-isopropyl-7,8-dipropoxy-5H-imidazo[2,1-a]isoindol-5-ol; and 5-(3,4-diethoxyphenyl)-2,3-dihydro-5H-imidazo[2,1-a]isoindol-5-ol.

EXAMPLE XI

Seventy grams of 9b-(p-tolyl)-1,2,3,9b-tetrahydro-1H-imidazo[2,1-a]isoindol-5-one and 300 ml. of 48 percent hydrobromic acid are stirred and heated to a clear solution. Stirring is continued for fifteen minutes after precipitation. Thereafter, the reaction mixture is cooled and the precipitated solid, 2-(2-aminoethyl)-3-(p-tolyl)-3-hydroxyphthalimidine hydrobromide, is separated by decantation, admixed with 40 g. of p-toluenesulfonyl chloride and 400 ml. of pyridine, heated to 100°C. for four hours and evaporated to dryness.

Twenty grams of the residue 9b-(p-tolyl)-1,2,3,9b-tetrahydro-1-(p-tolylsulfonyl)-1H-imidazo[2,1-a]isoindol-5-one are dissolved in 50 ml. of 80 percent sulfuric acid and stirred at room temperature for one hour. The reaction mixture which contains the sulfate salt of 2-(2-imidazolin-2-yl)-4'-methylbenzophenone is then cooled by the addition of ice water and made alkaline by the addition of a 10N sodium hydroxide solution. The precipitated solid is separated by decantation and recrystallized from dioxan to obtain crystalline 2,3-dihydro-5-(4-tolyl(-5H-imidazo[2,1-a]isoindol-5-ol, m.p. 208°–210°C.

In a similar manner, the following sulfates are synthesized: 4'-hexyl-2-(2-imidazolin-2-yl )benzophenone; 4-amino-2-(2-imidazolin-2-yl)benzaldehyde; 4'- chloro-2'-(2-imidazolin-2-yl)-2-phenylacetophenone; and 2-(2-imidazolin-2-yl)phenyl-2-thienyl ketone which are then contacted with a base to respectively afford the following: 5-(4-hexylphenyl)2,3-dihydro-5H-imidazo[2,1-a]isoindol-5-ol; 8-amino-2,3-dihydro-5H-imidazo[2,1-a]isoindol-5-ol; 8-chloro-5-(4-ethylphenyl)-2,3-dihydro-5H-imidazo[2,1-a]isoindol-5-ol; and 2,3-dihydro-5-(2-thienyl)-5H-imidazo[2,1-a]isoindol-5-ol.

EXAMPLE XII

Thirty-five grams of 9b-phenyl-1,2,3,9b-tetrahydro-1H-imidazo[2,1-a]isoindol-5-one and 150 ml. of 50 percent hydrochloric acid are stirred and heated to a clear solution. Stirring is continued for 30 minutes after solid begins to precipitate. The mixture is cooled and the solid is separated by filtration. On recrystallization from ethanol there is obtained 2-(2-aminoethyl)-3-phenyl-3-hydroxyphthalimidine hydrochloride.

Seventeen grams of the phthalimidine hydrochloride from above, 20 g. of p-butoxyphenylsulfonyl chloride and 200 ml. of pyridine are refluxed for two hours and then the mixture is evaporated to dryness. On recrystallization of the residue from ethanol there is obtained 9b-phenyl-1,2,3,9b-tetrahydro-1-(p-butoxyphenylsulfonyl)-1H-imidazo [2,1-a]isoindol-5-one which is admixed with 25 ml. of 95 percent sulfuric acid for one hour. The reaction mixture which contains the sulfate salt of 2-(2-imidazolin-2-yl) benzophenone is then cooled by the addition of ice water and made alkaline by the addition of a 5N potassium hydroxide solution. The product is then separated by filtration and recrystallized from dioxan to afford 2,3-dihydro-5-phenyl-5H-imidazo[2,1-a]isoindol-5-ol, m.p. 207 C., as a white crystalline solid which is insoluble in water and soluble in dimethylacetamide and ethanol.

Analysis: Ultra Violet Absorption (95% ETOH) infl. 225 m$\mu$ ($\epsilon$= 14,900), max. 268 m$\mu$ ($\epsilon$= 4,200); Ultra Violet Absorption (pH1) max. 250 m$\mu$ ($\epsilon$= 13,500); Infra Red Absorption (KBr) 1660 cm$^{-1}$, 2300–3000 cm$^{-1}$.

Calc'd for $C_{16}H_{14}N_2O$: C, 76.77; H, 5.63; N, 11.20 Found: C, 76.63; H, 5.66; N, 11.0.

Similarly, the sulfate salts of 2-(2-imidazolin-2-yl)-4-methylbenzophenone and 2-(2-imidazolin-2-yl)-6-propylbenzophenone are produced which are then converted to 2,3-dihydro-8-methyl-5-phenyl-5H-imidazo[2,1-a]isoindol-5-ol and 2,3-dihydro-5-phenyl-6-propyl-5H-imidazo[2,1-a]isoindol-5-ol.

EXAMPLE XIII

Forty grams of 9b-(p-bromophenyl)-1,2,3,9b-tetrahydro-1H-imidazo[2,1-a]isoindol-5-one and 200 ml. of 50 percent hydrochloric acid are stirred and heated to a clear solution. Stirring is continued for 20 minutes after solid begins to precipitate. The mixture is cooled and the solid is separated by filtration. On recrystallization from ethanol there is obtained 2-(2-aminoethyl)-3-(p-bromophenyl)-3-hydroxyphthalimidine hydrochloride.

Twenty grams of the phthalimidine hydrochloride from above, 24 g. of p-bromophenylsulfonyl chloride and 250 ml. of pyridine are refluxed for three hours and then the mixture is evaporated to dryness. On recrystallization of the residue from methanol there is obtained 9b-(p-bromophenyl)-1,2,3,9b-tetrahydro-1-(p-bromophenylsulfonyl)-1H-imidazo[2,1-a]isoindol-5-one which is hydrolyzed with sulfuric acid to afford the sulfate salt of 4'-bromo-2-(2-imidazolin-2-yl)benzophenone which is contacted with an aqueous sodium hydroxide solution. The product is then separated by filtration to afford 5-(4-bromophenyl)-2,3-dihydro-5H-imidazo[2,1-a]isoindol-5-ol, m.p. 194°–6°C., as a white crystalline solid which is soluble in dimethylacetamide and hot ethanol.

Analysis: Ultra Violet Absorption (95% ETOH) max. 228 m$\mu$ ($\epsilon$=15,300), max. 268 m$\mu$ ($\epsilon$=4,800), max. 274 m$\mu$ ($\epsilon$=4,800); Ultra Violet Absorption (pH1) max. 250 m$\mu$ (68=11,000), max. 270 m$\mu$ ($\epsilon$=10,500); Infra Red Absorption (KBr) 1660 c$^{-1}$, 2300-3000 c$^{-1}$.

Calc'd for $C_{16}H_{13}N_2OBr$: C, 58.38; H, 3.98; N, 8.50; Br, 24.28.

Found: C, 58.25; H, 4.02; N, 8.46; Br, 24.00.

In a similar manner, the following compounds are prepared:

3',4'-dichloro-2'-(2-imidazolin-2-yl)benzophenone sulfate which is neutralized to afford 5-(3,4-dichlorophenyl)-2,3-dihydro-5H-imidazo[2,1-a]isoindol-5-ol, m.p. 203–5°C., as a white crystalline solid which is soluble in hot dimethylacetamide and hot ethanol.

Analysis: Ultra Violet Absorption (95 /o ETOH), infl. 228 m$\mu$ ($\epsilon$=21,200), max. 274 m$\mu$ ($\epsilon$=4,500), max. 281 m$\mu$ ($\epsilon$=3,500); Ultra Violet Absorption (pH1) max. 243 m$\mu$ ($\epsilon$=12,200), max. 251 m$\mu$ ($\epsilon$=11,750), infl. 265 m$\mu$($\epsilon$=9,000), infl. 278 m$\mu$ ($\epsilon$=6,750); Infra Red Absorption (KBr) 1655 cm$^{-1}$, 2300–3000 cm$^{-1}$.

Calc'd for $C_{16}H_{12}Cl_2N_2O$: C, 60.21; H, 3.79; N, 8.78; Cl, 22.22. Found: C, 59.91; H, 3.66; N, 8.66; Cl, 22.30.

4'-fluoro-2 -(2-imidazolin-2-ylbenzophenone sulfate which is neutralized to afford 5-(4-fluorophenyl)-2,3-dihydro-5H-imidazo[2,1-a]isoindol-5-ol, m.p. 214°–216°C., dec., as a white crystalline solid which is insoluble in water and soluble in dimethylacetamide.

Analysis: Ultra Violet Absorption (95% ETOH), infl. 235 m$\mu$ ($\epsilon$= 12,000), infl. 242 m$\mu$ ($\epsilon$= 10,200), max. 263 m$\mu$ ($\epsilon$=6,100), max. 268 m$\mu$ ($\epsilon$=5,600); Ultra Violet Absorption (pH1) max. 251 ($\epsilon$= 13,000); Infra Red Absorption (KBr) 1640 cm$^{-1}$, 2300-3000cm$^{-1}$.

Calc'd for $C_{16}H_{13}N_2OF$: C, 71.62; H, 4.88; N, 10.44 Found: C, 71.73; H, 5.00; N, 10.68.

3'-bromo-4'-methyl-2-(2-imidazolin-2-yl)benzophenone sulfate which is neutralized to afford 5-(3-bromo-4-methylphenyl)-2,3-dihydro-5H-imidazo[2,1-a]isoindol-5-ol, m.p. 233°–5°C., dec., as a white crystalline solid which is insoluble in water and soluble in dimethylacetamide.

Analysis: Calcd for $C_{17}H_{15}BrN_2O$: C, 59.47; H, 4.41; N, 8.16; Br, 23.28. Found: C, 59.75; H, 4.60; N, 8.32; Br. 23.23.

EXAMPLE XIV

Ninety grams of 1,2,3,9b-tetrahydro-9b-phenyl-5H-imidazo[2,1-a]isoindol-5-one, 75 g. of p-toluenesulfonyl chloride and one liter of pyridine are heated at reflux for fourteen to eighteen hours. The solution is evaporated in vacuo to dryness, the residue slurried with water and then separated by filtration. On recrystallization from ethanol there is obtained 90 g. of 9b-phenyl-1,2,3,9b-tetrahydro-1-(p-tolysulfonl-5H-imidazo[2,1-a]isoindol-5-one, m.p. 158°–160°C.

Ninety grams of the above prepared sulfonamide compound is dissolved in 200 ml. of 80% sulfuric acid and is left at room temperature for two hours. The solution is diluted with two volumes of water and extracted with ether. The aqueous portion which contains the sulfate salt of 2-(2-imidazolin-2-yl)benzophenone is then neutralized with 50% sodium hydroxide solution while keeping the temperature below 25°C. The solid is separated and washed with water. On recrystallization from dimethylformamide there is obtained 27 g. of 2,3-dihydro-5-phenyl-5H-imidazo [2,1-a]isoindol-5-ol which has the same analytical characteristics as the product of Example XII.

EXAMPLE XV

Sixty grams of 9b-(4-chlorophenyl)-1,2,3,9b-tetrahydro-5H-imidazo[2,1-a]isoindol-5-one, 60 g. of p-toluenesulfonyl chloride and 750 ml. of pyridine are heated at reflux for fourteen hours. The reaction mixture is worked-up as described in Example XIV to obtain 70 g. of 9b-(p-chlorophenyl)-1,2,3,9b-tetrahydro-1-(p-tolylsulfonyl)-5H-imidazo [2,1-a]isoindol-5-one, m.p. 169°–171°C. which can be recrystallized from ethanol (m.p. 170°–2°C.).

Forth-five grams of the above prepared sulfonamide compound is dissolved in 100 ml. of 80% sulfuric acid and is left at room temperature for two hours. The solution is diluted with two volumes of water and extracted with ether. The aqueous portion which contains 4'-chloro-2-(2-imidazolin-2-yl)benzophenone is neutralized with 50% sodium hydroxide solution while keeping the temperature below 25°C. The solid is separated, washed with water and recrystallized from dimethylformamide to afford 23 g. of 5-(4-chlorophenyl)-2,3-dihydro-5H-imidazo[2,1-a]isoindol-5-ol which has the same analytical characteristics as the product of Example X.

The above procedure is repeated to react a 1,2,3,9b-tetrahydro-1H-imidazo[2,1-a]isoindol-5-one of VIII-–XII with an appropriate sulfonyl halide, in pyridine, at a temperature within the range of about 80°C. to above 115 C. for a period of about two to about ten hours to afford the corresponding sulfonamide which is treated with about 80 to about 100 percent sulfuric acid to yield an appropriate 2-(2-imidazolin-2-yl)benzophenone sulfate which is neutralized to produce a 2,3-dihydro-5H-imidazo[2,1-a] isoindol-5-ol.

EXAMPLE XVI

Ten grams of 2,3-dihydro-5-phenyl-5H-imidazo[2,1-a] isoindol-5-ol, as described in Example XII, are suspended in 75 ml. of absolute ethanol and then saturated with a continuous flow of hydrochloric acid gas. The resulting solution is filtered to remove impurities and on standing 2-(2-imidazolin-2-yl)benzophenone hydrochloride precipitates as a white crystalline sold, m.p. 197°–9°C., dec.

Analysis: Ultra Violet Absorption (95% ETOH) max. 250 m$\mu$($\epsilon$= 12,800); Infra Red Absorption (KBr) 1647 cm$^{-1}$, 2400–3200 cm$^{-1}$.

Calc'd for $C_{16}H_{14}N_2O \cdot HCl$: C, 67.03; H, 5.27; N, 9.77; Cl, 12.36. Found: C, 66.88; H, 5.33; N, 9.83; Cl, 12.50.

EXAMPLE XVII

Ten grams of 5-(4-chlorophenyl)-2,3-dihydro-5H-imidazo[2,1-a]iscindol-5-ol, as described in Example X, are suspended in 75 ml. of absolute ethanol and then saturated with a continuous flow of hydrochloric acid gas. The resulting solution is filtered, evaporated to dryness and the residue recrystallized from ethanol-ethyl acetate to afford 4'-chloro-2-(2-imidazolin-2-yl)benzophenone hydrochloride, m.p. 170°–2°C., dec., as a white crystalline solid which is soluble in water.

Analysis: Ultra Violet Absorption (95% ETOH) infl. 223 m$\mu$ ($\epsilon$ = 19,100), max. 252 m$\mu$ ($\epsilon$ = 12,100), max. 265 m$\mu$ ($\epsilon$ = 12,300); Infra Red Absorption (KBr) 1647 cm$^{-1}$, 2300–3200 cm$^{-1}$.

Calc'd for $C_{16}H_{13}N_2OCl \cdot HCl$: C, 59.80; H, 4.40; N, 8.72; Cl, 22.08. Found: C, 59.63; H, 4.50; N, 8.72; Cl, 21.79.

Similarly, the following hydrochlorides are prepared:

2-(2-imidazolin-2-yl)-3',4'-diiodobenzophenone hydrochloride;

2'-(2-imidazolin-2-yl)-2-methyl-4',5'-dipropoxypropiophenone hydrochloride;

3',4'-diethoxy-2-(2-imidazolin-2-yl)benzophenone hydrochloride;

2-(2-imidazolin-2-yl)-4'-methylbenzophenone hydrochloride;

4'-hexyl-2-(2-imidazolin-2-yl)benzophenone hydrochloride;

4-amino-2-(2-imidazolin-2-yl)benzaldehyde dihydrochloride;

4-chloro-2-(2-imidazolin-2-yl)-2'-phenylacetophenone hydrochloride;

2-(2-imidazolin-2-yl)phenyl-2-thienyl ketone hydrochloride;

2-(2-imidazolin-2-yl)-4-methylbenzophenone hydrochloride;

2-(2-imidazolin-2-yl)-6-propylbenzophenone hydrochloride;

4'-bromo-2-(2-imidazolin-2-yl)benzophenone hydrochloride;

3',4'-dichloro-2-(2-imidazolin-2-yl)benzophenone hydrochloride;

4'-fluoro-2-(2-imidazolin-2-yl)benzophenone hydrochloride; and

3'-bromo-2-(2-imidazolin-2-yl)-4'-methylbenzophenone hydrochloride.

EXAMPLE XVIII

When the procedure of Examples X – XV are repeated with appropriate starting material, the following dihydroimidazoisoindolols are prepared which by the procedure described in Examples XVI – XVII are then converted to their corresponding imidazolinyl phenyl carbonyl hydrochlorides.

| DIHYDROIMIDAZOISOINDOLOLS | IMIDAZOLINYL PHENYL CARBONYL HYDROCHLORIDE |
|---|---|
| 7-bromo-2,3-dihydro-5-(4-tolyl)-5H-imidazo[2,1-a]isoindol-5-ol | 5-bromo-2-(2-imidazolin-2-yl)-4-methylbenzophenone hydrochloride |
| 2,3-dihydro-8-methyl-5-propyl-5H-imidazo[2,1-A]isoindol-5-ol | 2-(2-imidazolin-2-yl)-4-methylbutyrophenone hydrochloride |
| 2,3-dihydro-9-iodo-5H-imidazo[2,1-a]isoindol-5-ol | 2-(2-imidazolin-2-yl)-3-iodobenzaldehyde hydro- |

| DIHYDROIMIDAZOISOINDOLOLS | IMIDAZOLINYL PHENYL CARBONYL HYDROCHLORIDE |
|---|---|
| 7,8-dibromo-5-(4-bromophenyl)-2,3-dihydro-5H-imidazo[2,1-a]isoindol-5-ol | chloride 4,4',5-tribromo-2-(2-imidazolin-2 yl)benzophenone hydrochloride |
| 2,3-dihydro-5-(2,4-dimethoxyphenyl)-5H-imidazo[2,1-a]isoindol-5-ol | 2-(2-imidazolin-2-yl)-2',4'-dimethoxybenzophenone hydrochloride |
| 5-(2,4-dibromophenyl)-2,3-dihydro-5H-imidazole[2,1-a]isoindol-5-ol | 2',4'-dibromo-2-(2-imidazolin-2-yl)benzophenone hydrochloride |
| 2,3-dihydro-5-(5,6,7,8-tetrahydro-2-naphthyl)-5H-imidazo[2,1-a]isoindol-5-ol | 2-(2-imidazolin-2-yl) phenyl-(5,6,7,8-tetrahydro-2-naphthyl)ketone hydrochloride |
| 5-(4-trifluoromethylphenyl)-2,3-dihydro-5H-imidazo[2,1-a]isoindol-5-ol | 4'-trifluoromethyl-2-(2-imidazolin-2-yl)benzophenone hydrochloride |
| 5-(2-trifluoromethylphenyl)-2,3-dihydro-5H-imidazo[2,1-a]isoindol-5-ol | 2'-trifluoromethyl-2-(2-imidazolin-2-yl)benzophenone hydrochloride |
| 5-furyl-2,3-dihydro-5H-imidazo[2,1-a]isoindol-5-ol | furyl-2-(2-imidazolin-2-yl) phenyl ketone hydrochloride |
| 2,3-dihydro-5-methyl-5H-imidazo[2,1-a]isoindol-5-ol | 2-(2-imidazolin-2-yl)acetophenone hydrochloride |
| 2,3-dihydro-5H-imidazo[2,1-a]isoindol-5-ol | 2-(2-imidazolin-2-yl)benzaldehyde hydrochloride |
| 5-benzyl-2,3-dihydro-5H-imidazo[2,1-a]isoindol-5-ol | 2'-(2-imidazolin-2-yl)-2-phenylacetophenone hydrochloride |
| 5-butyl-2,3-dihydro-5H-imidazo[2,1-a]isoindol-5-ol | 2-(2-imidazolin-2-yl)valerophenone hydrochloride |
| 5-(3-amino-4-chlorophenyl)-2,3-dihydro-5H-imidazo[2,1-a]isoindol-5-ol | 3'-amino-4'-chloro-2-(2-imidazolin-2-yl)benzophenone dihydrochloride |
| 7-chloro-2,3-dihydro-5-phenyl-5H-imidazo[2,1-a]isoindol-5-ol | 5-chloro-2-(2-imidazolin-2-yl)benzophenone hydrochloride |
| 2,3-dihydro-8-methyl-5-phenyl-5H-imidazo[2,1-a]isoindol-5-ol | 2-(2-imidazolin-2-yl)-4-methylbenzophenone hydrochloride |
| 7-ethylamino-2,3-dihydro-5-phenyl-5H-imidazo[2,1-a]isoindol-5-ol | 5-ethylamino-2-(2-imidazolin-2-yl)benzophenone dihydrochloride |
| 7,8-dichloro-2,3-dihydro-5-phenyl-5H-imidazo[2,1-a]isoindol-5-ol | 4,5-dichloro-2-(2-imidazolin-2-yl)benzophenone hydrochloride |
| 2,3-dihydro-7,8-dimethoxy-5-phenyl-5H-imidazo[2,1-a]isoindol-5-ol | 2-(2-imidazolin-2-yl)-4,5-dimethoxybenzophenone hydrochloride |
| 2,3-dihydro-5-(3-iodophenyl)-5H-imidazo[2,1-a]isoindol-5-ol | 2-(2-imidazolin-2-yl)-3'-iodobenzophenone hydrochloride |
| 8-amyl-2,3-dihydro-5-phenyl-5H-imidazo[2,1-a]isoindol-5-ol | 4-amyl-2-(2-imidazolin-2-yl)benzophenone hydrochloride |
| 2,3-dihydro-5-phenyl-7-propyl-5H-imidazo[2,1-a]isoindol-5-ol | 2-(2-imidazolin-2-yl)-5-propylbenzophenone hydrochloride |
| 8-butoxy-2,3-dihydro-5-phenyl-5H-imidazo[2,1-a]isoindol-5-ol | 4-butoxy-2-(2-imidazolin-2-yl)benzophenone hydrochloride |
| 2,3-dihydro-5-(3,4-dimethylphenyl)-5H-imidazo[2,1-A]isoindol-5-ol | 2-(2-imidazolin-2-yl)-3',4'-dimethylbenzophenone hydrochloride |
| 2,3-dihydro-5-(4-propoxyphenyl)-5H-imidazo[2,1-a]isoindol-5-ol | 2-(2-imidazolin-2-yl)-4'-propoxybenzophenone hydrochloride |
| 2,3-dihydro-7,8-dimethyl-5H-imidazo[2,1-a]isoindol-5-ol | 2-(2-imidazolin-2-yl)-4,5-dimethylbenzaldehyde hydrochloride |

EXAMPLE XIX 2-(2-Imidazolin-2-yl)benzophenone hydrobromide is prepared by admixing an ethanolic solution of 2,3-dihydro-5-phenyl-5H-imidazo[2,1-a]isoindol-5-ol with an ethanol solution containing an equivalent amount of hydrobromic acid and, thereafter, evaporating the solvent under vacuum.

Other new tetrahydropyrimidinyl phenyl carbonyl imidazolinyl carbonyl carbonly and tetrahydropyrimidoisoindolol acid addition salts of the present invention are prepared by the same procedure employing hydrobromic acid, hydroiodic acid, nitric acid, sulfuric acid, phosphoric acid, acetic acid, lactic acid, citric acid, tartaric acid, maleic acid and gluconic acid.

EXAMPLE XX

Two grams of 1-(p-chlorophenyl)-1,2,3,4,5,6-hexahydro-2,5-benzodiazocine dihydrochloride are dissolved in 50 ml. of water. A solution of 1 g. of potassium permanganate in 50 ml. of water is added dropwise over a period of one-half hour. The mixture is filtered to remove inorganic salts and the filtrate is made basic with sodium carbonate solution. The precipitated solid is separated and washed with water. On recrystallization from ethanol there is obtained 5-(4-chlorophenyl)-2,3-dihydro-5H-imidazo [2,1-a]isoindol-5-ol which has the same physical characteristics as the identical compound of Example X.

Similarly, 2,3-dihydro-5-(2-phenethyl-5H-imidazo[2,1-a]isoindol-5-ol is obtained by the oxidation of 1-phenethyl-1,2,3,4,5,6-hexahydro-2,5-benzodiazocine dihydrobromide with potassium dichromate.

EXAMPLE XXI

Repeating the procedure of Example XX to oxidize a hereinafter listed hexahydrobenzodiazocine, the following dihydroimidazoisoindolol compounds are prepared:

| HEXAHYDROBENZODIAZOCINE | DIHYDROIMIDAZOISOINDOLOLS |
|---|---|
| 1,2,3,4,5,6-hexahydro-1-(p-bromophenyl)-2,5-benzodiazocine dihydrochloride | 5-(4-bromophenyl)-2,3-dihydro-5H-imidazo[2,1-a]isoindol-5-ol |
| 1,2,3,4,5,6-hexahydro-1-(p-methoxyphenyl)-2,5-benzodiazocine dihydrochloride | 2,3-dihydro-5-(4-methoxyphenyl)-5H-imidazo[2,1-a]isoindol-5-ol |
| 1-benzyl-1,2,3,4,5,6-hexahydro-2,5-benzodiazocine dihydrobromide | 5-benzyl-2,3-dihydro-5H-imidazo[2,1-a]isoindol-5-ol |
| 1,2,3,4,5,6-hexahydro-1-(2-thienyl)-2,5-benzodiazocine dihydrochloride | 2,3-dihydro-5-(2-thienyl)-5H-imidazo[2,1-a]isoindol-5-ol |
| 1-(3-furyl)-1,2,3,4,5,6-hexahydro-2,5-benzodiazocine dihydrochloride | 5-(3-furyl)-2,3-dihydro-5H-imidazo[2,1-a]isoindol-5-ol |
| 1,2,3,4,5,6-hexahydro-8-methyl-1-phenyl-2,5-benzodiazocine dihydrochloride | 2,3-dihydro-7-methyl-5-phenyl-5H-imidazo[2,1-a]isoindol-5-ol |
| 1,2,3,4,5,6-hexahydro-1-(2-pyridyl)-2,5-benzodiazocine dihydrochloride | 2,3-dihydro-5-(2-pyridyl)-5H-imidazo[2,1-a]isoindol-5-ol |
| 1,2,3,4,5,6-hexahydro-8,9dimethoxy-1-(p-tolyl)-2,5-benzodiazocine dihydrochloride | 2,3-dihydro-7,8-dimethoxy-5-(4-tolyl)-5H-imidazo[2,1-a]isoindol-5-ol |

EXAMPLE XXII

Four grams of 1,2,3,4,5,6-hexahydro-8,9-dimethyl1-phenyl-2,5-benzodiazocine is dissolved in 100 ml. of acetone. A solution of 2 g. of potassium chlorate in 100 ml. of water is added dropwise over a period of an hour. Thereafter, the mixture is filtered and evaporated to dryness to afford 2,3-dihydro-7,8-dimethyl-5H-imidazo[2,1-a]isoindol-5-ol which is recrystallized from methanol.

Simiarly, 1-ethyl-1,2,3,4,5,6-hexahydro-2,5-benzodiazocine is oxidized to afford 5-ethyl-2,3-dihydro-5H-imidazo[2,1-a]isoindol-5-ol.

EXAMPLE XXIII

One gram of 1,2,3,4,5,6-hexahydro-1-phenyl-2,5-benzodiazocine dihydrochloride is dissolved in 25 ml. of water. A solution of 0.5 g. of potassium permanganate in 25 ml. of water is added over a period of one hour. The mixture is filtered to remove precipitated inorganic salts and the filtrate is made alkaline with a potassium bicarbonate solution. The precipitated product is separated and recrystallized from ethanol. The product obtained in this manner is 2,3-dihydro-5-phenyl-5H-imidazo[2,1-a]isoindol-5-ol which has the same physical characteristics as the identical compound of Example XII.

In the same manner, 1,2,3,4,5,6-hexahydro-1-(2,4-dimethoxyphenyl)-2,5-benzodiazocine is converted to 2,3-dihydro-5-(2,4-dimethoxyphenyl)-5H-imidazo[2,1-a]isoindol-5-ol.

EXAMPLE XXIV

When the oxidation procedures of the previous Examples are repeated at temperature ranges from 20°C. to 60°C. for periods of up to about four hours on the following hexahydrobenzodiazocines the hereinafter listed dihydroimidazoisoindolol compounds are obtained:

| HEXAHYDROBENZODIAZOCINES | DIHYDROIMIDAZOISOINDOLOLS |
|---|---|
| 1,2,3,4,5,6-hexahydro-1-(5,6,7,8-tetrahydro-2-naphthyl)-2,5-benzodiazocine | 2,3-dihydro-5-(5,6,7,8-tetrahydro-2-naphthyl)-5H-imidazo[2,1-a]isoindol-5-ol |
| 1,2,3,4,5,6-hexahydro-1-(p-trifluoromethylphenyl)-2,5-benzodiazocine | 5-(4-trifluoromethylphenyl)-2,3-dihydro-5H-imidazo[2,1-a]isoindol-5-ol |
| 1,2,3,4,5,6-hexahydro-8,9-dichloro-1-phenyl-2,5-benzodiazocine | 7,8-dichloro-2,3-dihydro-5-phenyl-5H-imidazo[2,1-a]isoindol-5-ol |
| 1-(p-ethylphenyl)-1,2,3,4,5,6-hexahydro-2,5-benzodiazocine | 5-(4-ethylphenyl)-2,3-dihydro-5H-imidazo[2,1-a]isoindol-5-ol |
| 8,9-dibromo-1,2,3,4,5,6-hexahydro-1-phenyl-2,5-benzodiazocine | 7,8-dibromo-2,3-dihydro-5-phenyl-5H-imidazo[2,1-a]isoindol-5-ol |
| 1,2,3,4,5,6-hexahydro-9-methylamino-1-(p-tolyl)-2,5-benzodiazocine | 2,3-dihydro-8-methylamino-5-(4-tolyl)-5H-imidazol[2,1-a]isoindol-5-ol |

EXAMPLE XXV

Ten grams of 1-(3,4-dichlorophenyl)-1,2,3,4,5,6-hexahydro-2,5-benzodiazocine dihydrochloride are dissolved in 250 ml. of water. A solution of 5.0 g. of potassium permanganate in 250 ml. of water is added over a period of two hours. The mixture is filtered to remove precipitated inorganic salts and the filtrate is made alkaline with a sodium bicarbonate solution. The precipitated product is separated and recrystallized from methanol. The product obtained in this manner is 5-(3,4-dichlorophenyl)-2,3-dihydro-5H-imidazo[2,1-a]isoindol-5-ol which has the same physical characteristics as the identical compound of Example XIII.

Similarly, 1-(3,4-dibromophenyl)-1,2,3,4,5,6-hexahydro-9-methyl-2,5-benzodiazocine dihydrobromide is oxidized to afford 5-(3,4-dibromophenyl)-2,3-dihydro-8-methyl-5H-imidazo[2,1-a]isoindol-5-ol.

EXAMPLE XXVI

When the oxidation procedure of Examples XX to XXV is repeated employing the following hexahydrobenzodiazocines as starting materials, the hereinafter listed dihydroimidazoisoindolol compounds are produced.

| HEXAHYDROBENZODIAZOCINES | DIHYDROIMIDAZOISOINDOLOLS |
|---|---|
| 1-(p-ethoxyphenyl)-1,2,3,4,5,6-hexahydro-2,5-benzodiazocine | 5-(4-ethoxyphenyl)-2,3-dihydro-5H-imidazo[2,1-a]isoindol-5-ol |
| 1,2,3,4,5,6-hexahydro-1,9-dimethyl-2,5-benzodiazocine | 2,3-dihydro-5,8-dimethyl-5H-imidazo[2,1-a]isoindol-5-ol |
| 8-ethyl-1,2,3,4,5,6-hexahydro-1-phenyl-2,5-benzodiazocine | 7-ethyl-2,3-dihydro-5-phenyl-5H-imidazo[2,1-a]isoindol-5-ol |
| 1,2,3,4,5,6-hexahydro-8,9-dimethyl-1-phenethyl-2,5-benzodiazocine | 2,3-dihydro-7,8-dimethyl-5-(2-phenethyl)-5H-imidazo[2,1-a]isoindol-5-ol |
| 8-fluoro-1,2,3,4,5,6-hexahydro-1-(p-tolyl)-2,5-benzodiazocine | 7-fluoro-2,3-dihydro-5-(4-tolyl)-5H-imidazo[2,1-a]isoindol-5-ol |

What is claimed is:

1. A process for the preparation of acid addition salts having the formula:

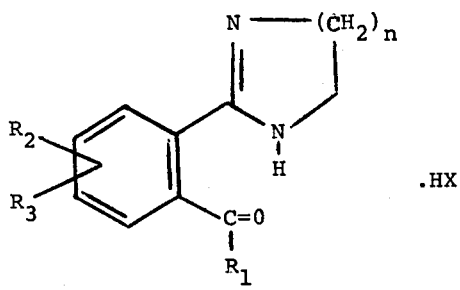

wherein $R_1$ is selected from the group consisting of hydrogen, lower alkyl, phen(lower)alkyl, phenyl, monohalophenyl, dihalophenyl, mono(lower)alkylphenyl, di(lower)alkylphenyl, trifluoromethylphenyl, mono(lower)alkoxyphenyl, di(lower)alkoxyphenyl, thienyl, pyridyl, furyl and tetrahydro-2-naphthyl; $R_2$ is selected from the group consisting of hydrogen, halogen, amino, lower alkylamino, lower alkyl and lower alkoxy; $R_3$ is hydroxy when $R_2$ and $R_3$ are dissimilar and when $R_2$ and $R_3$ are the same they are both selected from the group consisting of phenyl, monohalophenyl, dihalophenyl, mono(lower)alkylphenyl, di(lower)alkylphenyl, trifluoromethylphenyl, mono(lower)alkoxyphenyl, di(lower)alkoxyphenyl, thienyl, pyridyl, furyl and tetrahydro-2-naphthyl; n is 1; and HX is a pharmacologically acceptable acid, which comprises reacting a compound having the formula:

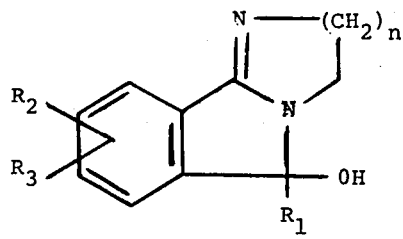

wherein $R_1$, $R_2$, $R_3$ and n are defined as above, with a pharmacologically acceptable acid in ethanolic solution.

2. A process according to claim 1 wherein the reaction occurs in an aqueous solution.

* * * * *

UNITED STATES PATENT AND TRADEMARK OFFICE
CERTIFICATE OF CORRECTION

PATENT NO. : 3,935,218

DATED : January 27, 1976

INVENTOR(S) : Theodore S. Sulkowski

It is certified that error appears in the above-identified patent and that said Letters Patent are hereby corrected as shown below:

Column 8, line 65: imidazoline portion of structure is lacking an NH group. Should be:

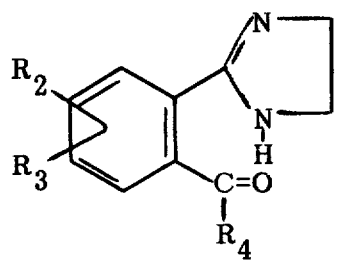

Signed and Sealed this

Sixth Day of March 1979

[SEAL]

Attest:

RUTH C. MASON
Attesting Officer

DONALD W. BANNER
Commissioner of Patents and Trademarks